(12) United States Patent
Dahmani et al.

(10) Patent No.: US 11,266,787 B2
(45) Date of Patent: Mar. 8, 2022

(54) DRUG DELIVERY ASSEMBLY FOR CARTRIDGE-BASED MEDICAMENTS

(71) Applicant: QuiO Technologies LLC, Chicago, IL (US)

(72) Inventors: Alexander Dahmani, New York, NY (US); Jared Schwartzentruber, New York, NY (US)

(73) Assignee: QuiO Technologies LLC, New York, NY (US)

( * ) Notice: Subject to any disclaimer, the term of this patent is extended or adjusted under 35 U.S.C. 154(b) by 359 days.

(21) Appl. No.: 16/315,071

(22) PCT Filed: Jul. 5, 2017

(86) PCT No.: PCT/US2017/040671
§ 371 (c)(1),
(2) Date: Feb. 22, 2019

(87) PCT Pub. No.: WO2018/009509
PCT Pub. Date: Jan. 11, 2018

(65) Prior Publication Data
US 2019/0388621 A1 Dec. 26, 2019

Related U.S. Application Data

(60) Provisional application No. 62/358,751, filed on Jul. 6, 2016.

(51) Int. Cl.
*A61M 5/315* (2006.01)
*A61M 5/20* (2006.01)
(Continued)

(52) U.S. Cl.
CPC ...... *A61M 5/31546* (2013.01); *A61M 5/2033* (2013.01); *A61M 5/31568* (2013.01);
(Continued)

(58) Field of Classification Search
CPC ................ A61M 5/20; A61M 5/31545; A61M 5/31546; A61M 5/3155; A61M 2005/2013; A61M 2005/31588; A61M 2005/31568
See application file for complete search history.

(56) References Cited

U.S. PATENT DOCUMENTS 6,454,746 B1 * 9/2002 Bydlon ............... A61M 5/3137
604/227
6,585,698 B1 7/2003 Packman et al.
(Continued)

FOREIGN PATENT DOCUMENTS

WO    WO 99/44657    9/1999
WO    WO 02/074369    9/2002
(Continued)

OTHER PUBLICATIONS

International Search Report and Written Opinion dated Nov. 21, 2017 for International Application No. PCT/US2017/040671.

*Primary Examiner* — Laura A Bouchelle
(74) *Attorney, Agent, or Firm* — Perkins Coie LLP (57) ABSTRACT

Embodiments of the present disclosure describe drug delivery with a reusable pen injector. In particular, several embodiments are directed to motor-driven delivery of cartridge-based medicaments with an electronic pen injector device and associated pen cap device.

15 Claims, 10 Drawing Sheets

(51) Int. Cl.
*A61M 5/32* (2006.01)
*A61M 5/46* (2006.01)

(52) U.S. Cl.
CPC ...... *A61M 5/31585* (2013.01); *A61M 5/3202* (2013.01); *A61M 5/3234* (2013.01); *A61M 5/46* (2013.01); *A61M 2005/206* (2013.01); *A61M 2005/2013* (2013.01); *A61M 2205/3303* (2013.01); *A61M 2205/3327* (2013.01); *A61M 2205/3368* (2013.01); *A61M 2205/50* (2013.01); *A61M 2205/52* (2013.01); *A61M 2205/8206* (2013.01)

(56) References Cited

U.S. PATENT DOCUMENTS

| | | |
|---|---|---|
| 8,784,372 B1 | 7/2014 | Hoggatt |
| 2011/0137286 A1 | 6/2011 | Mudd et al. |
| 2011/0282173 A1 | 11/2011 | Fonduca et al. |
| 2012/0056019 A1* | 3/2012 | Renz ............ A61M 5/24 239/584 |
| 2013/0204224 A1 | 8/2013 | Muller-Pathle et al. |
| 2014/0018733 A1 | 1/2014 | Sjolund et al. |
| 2015/0290396 A1 | 10/2015 | Nagar et al. |
| 2016/0058952 A1 | 3/2016 | Sanofi |

FOREIGN PATENT DOCUMENTS

| | | |
|---|---|---|
| WO | WO 2010/056712 | 5/2010 |
| WO | WO 2011/067187 | 6/2011 |
| WO | WO 2016/011207 | 1/2016 |
| WO | WO 2016/020276 | 2/2016 |

\* cited by examiner

Fig 9b

DRUG DELIVERY ASSEMBLY FOR CARTRIDGE-BASED MEDICAMENTS

PRIORITY CLAIM

This application is a 35 U.S.C. § 371 U.S. National Stage Application of International Application No. PCT/US2017/040671 filed Jul. 5, 2017, which claims priority to U.S. Provisional Patent Application Ser. No. 62/358,751 which was filed on Jul. 6, 2016, the entire contents of which are incorporated herein by reference and relied upon.

TECHNICAL FIELD

The present disclosure relates to drug delivery with a reusable pen injector device. In particular, several embodiments are directed to motor-driven delivery of cartridge-based medicaments with an electronic pen injector device and associated pen cap device.

BACKGROUND

Patients suffering from diabetes must frequently inject themselves with medicament. A variety of drug delivery devices known as pen injectors have been developed to enable a person to conveniently and reliably self-inject medicament. These devices accept a cartridge containing multiple doses of a liquid medicament. Pen injectors are often furnished with a linear actuator that is axially movable to advance the plunger in the cartridge. Forward movement of the plunger within the cartridge results in the medicament being dispensed from an outlet on the cartridge end opposite of the plunger and drive mechanism.

SUMMARY

One advantage of the present technology is that a pen injector can be provided with an electronic drive mechanism that can reliably deliver a medicament with multiple controlled speeds.

Another advantage of the present technology is that a pen injector can be provided with an electronic drive mechanism that will never deliver a volume of medicament larger than what the patient selected.

Still another advantage of the present technology is that a pen cap can be provided with batteries that can supply energy when connected to an electronic pen injector, increasing the overall battery life of the drug delivery assembly.

Still another advantage of the present technology is that a pen cap can be provided with a housing capable of hiding the needle during injection when connected to a pen injector.

Still another advantage of the present technology is that a pen cap can be provided with a housing capable of facilitating needle insertion to the appropriate tissue depth when connected to a pen injector.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. For ease of reference, throughout this disclosure identical reference numbers may be used to identify identical or at least generally similar or analogous components or features.

DETAILED DESCRIPTION

Various embodiments of the present disclosure relate to a drug delivery assembly including a reusable pen injector device and an associated pen cap device. The electronic pen injector device and associated pen cap device allow for the motor-driven delivery of cartridge-based medicaments, among other features as described herein.

In the present disclosure, reference is primarily made to delivery of insulin for treatment of diabetes; however, this is only an exemplary use of the technology described in the present disclosure.

Conventional pen injectors are often disposable. Disposable pen injectors are pre-loaded with a filled cartridge, and can only be used until the cartridge runs out of medicament. Reusable pen injectors are becoming more common, because additional features can be cost-effectively incorporated into a device that is used long-term. One beneficial feature is electronic recording of injections. This helps a patient track their medicament consumption during normal use of the pen injector. Another beneficial feature is wireless connectivity for transmitting the electronic injection recordings.

Many conventional reusable pen injectors incorporate a battery and a processor in order to achieve the valuable features described above. However, despite the presence of electronics, these reusable pen injectors often employ a mechanical drive mechanism for advancing the plunger in the cartridge to dispense the medicament. PCT Publication Number WO201011257 discloses one such reusable pen injector with electronic components and a purely mechanical drive mechanism. One problem with a reusable mechanical pen injector is the complexity in parts required to reliably deliver a medicament throughout the life of the pen injector. Another problem is the resetting mechanism when a cartridge is changed. The patient is typically required to push the actuator back into the pen injector, which can lead to damage and user errors.

Alternatively to a mechanical drive mechanism, an electromechanical drive mechanism may be used. An electromechanical drive mechanism typically includes an electric motor for moving the linear actuator and advancing the plunger in the cartridge. PCT Publication Number WO2015044102 discloses a reusable pen injector with such an electromechanical drive mechanism. The motor-driven actuation system has several advantages over a mechanical drive mechanism. It can be appreciated from the drawings how many fewer parts are necessary in an electromechanical drive mechanism compared to purely mechanical. The motor provides a host of additional benefits, including automation of the actuator reset during cartridge replacement. Another advantage is more consistent flow rates and injection durations because the motor can overcome variable tissue pressures and drug temperatures. The motor also enables multiple injection speeds to be selected by the user based on their comfort preference.

However, motor-driven pen injectors like the one described above can be very dangerous. The motor is controlled by software, which inherently has several vulnerabilities, including bugs and malware. The most critical danger is delivery of an inappropriately large dose by the pen injector. For a drug like insulin, this is a potentially lethal event.

There is also the issue of battery life for electronic pen injectors. Pen injectors are preferably slim and compact for patients to use on the go. This limits the size and number of batteries that can be integrated into the device, thus limiting the overall battery life. Battery life may be even more limited for pen injectors with electromechanical drive mechanisms.

There are additional deficiencies that affect conventional pen injectors. Since cartridges contain multiple doses of medicament, a pen injector must facilitate needle replacement for each injection. This design constraint results in the needle being visible during the injection process. It also requires the user to manually insert the needle into his/her tissue in order to inject. This is a source of anxiety for many patients, and can lead to user error and poor medication adherence.

Thus, the technology described in the present disclosure provides a drug delivery assembly that can overcome one or more of these deficiencies.

Specific details of several embodiments of the technology are described below with reference to FIGS. 1A-9B. Although many of the embodiments are described below with respect to devices, systems, and methods for controlled delivery of medicament into a subject, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1A-9B.

Selected Examples of Automatic Injectors and Related Devices

Figure 1A:
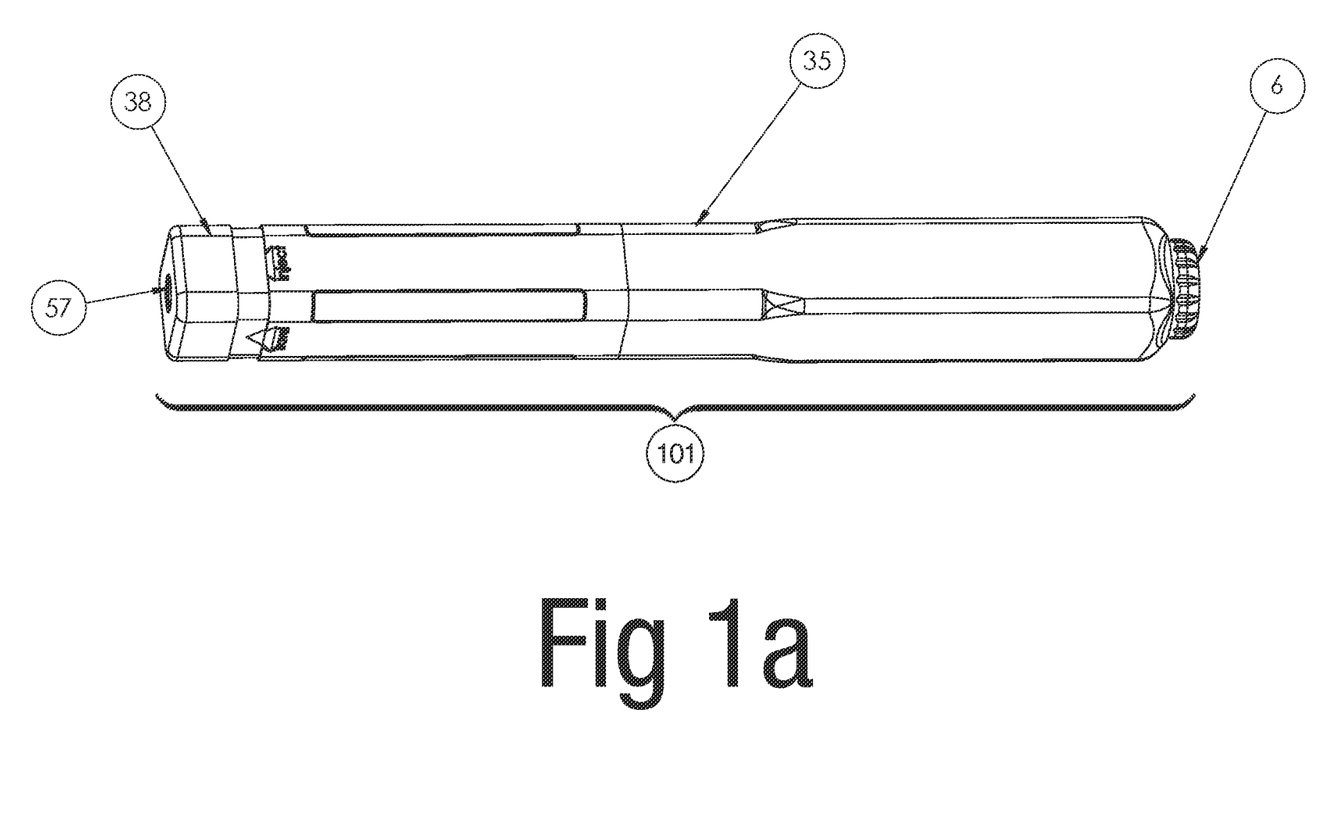
FIGS. 1A and 1B are a front-side view of the drug delivery assembly that includes a pen injector with and without a pen cap operatively connected, respectively, in accordance with an embodiment of the present technology.
Figure 1B:
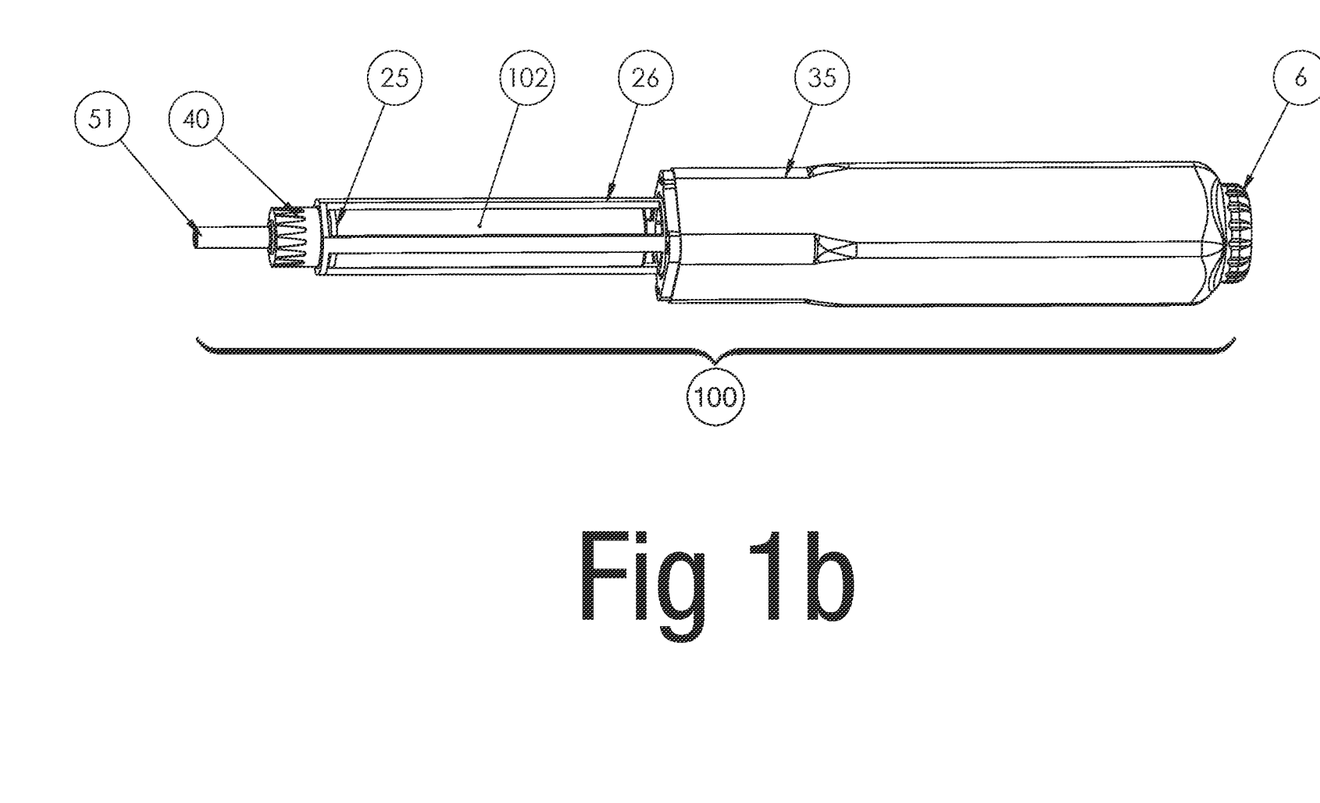

FIGS. 1A and 1B are front-side views of a drug delivery assembly 101, including a pen injector 100 with and without a pen cap 38, respectively, the drug delivery assembly being used to inject a medicament 102 within a cartridge 25 by way of a hypodermic needle 40, in accordance with an embodiment of the present technology. The pen injector 100 comprises a base 35 and a cartridge holder 26. The injector 100 can house a cartridge 25 within the cartridge holder 26. In some embodiments, the cartridge holder is loaded by detaching it from the base 35 and loading a cartridge 25 vertically into the cartridge holder 26. In some embodiments, a needle is attached to the distal end of the cartridge holder 26, forming a fluid pathway with the distal end of the cartridge. The pen cap 38 can be attached to the base 35, physically covering the cartridge holder 26. In some embodiments, the cap 38 can only be attached to the base 35 when a needle is not attached to the cartridge holder 26. In another embodiment, the cap 38 can be attached to the base 35 when a needle is attached to the cartridge 25. In some embodiments, the pen injector 100 can be used to inject the medicament 102 while the cap 38 is operatively connected to the base 35. The pen injector 100 can also be used while the cap 38 is detached from the base 35.

Figure 2:
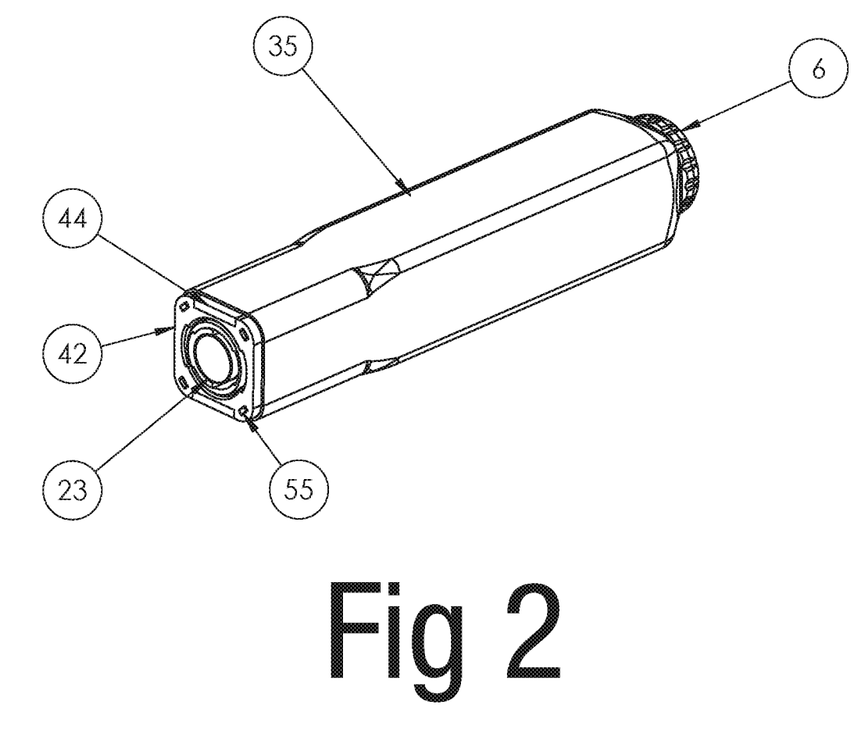
FIG. 2 is a front-side view of the pen injector base, in accordance with an embodiment of the present technology.

FIG. 2 is a front-side view of the base 35 of the pen injector 100, including a dial 6 to allow user input in accordance with an embodiment of the present technology. In certain embodiments, the dial 6 can move axially, providing at least two distinct positions and can rotate radially to allow further user input. While the dial 6 is shown as a rotatable selection mechanism in FIG. 2, it should be understood that other types of selection mechanisms may be used. In certain embodiments, the cartridge connect 42 provides a method for operatively connecting the cartridge holder 26 to the base 35. The cartridge connect 42 provides concentric positioning of the plunger head 23 and the lead screw nut 22. The cartridge connect 42 prevents radial motion and a distal stop of the lead screw nut 22. The base 35 includes a cap connect 55, which provides a method for operatively connecting to the pen cap 38 when the pen cap 38 is fully covering the cartridge holder 26. In certain embodiments, the cap connect 55 concentrically surrounds the cartridge connect 42 on the distal end of the base 35. The cap connect 55 secures the pen cap 38 in place through mechanical connections. In some embodiments, the cap connect 55 also forms an electrical connection with the pen cap 38.

Figure 3:
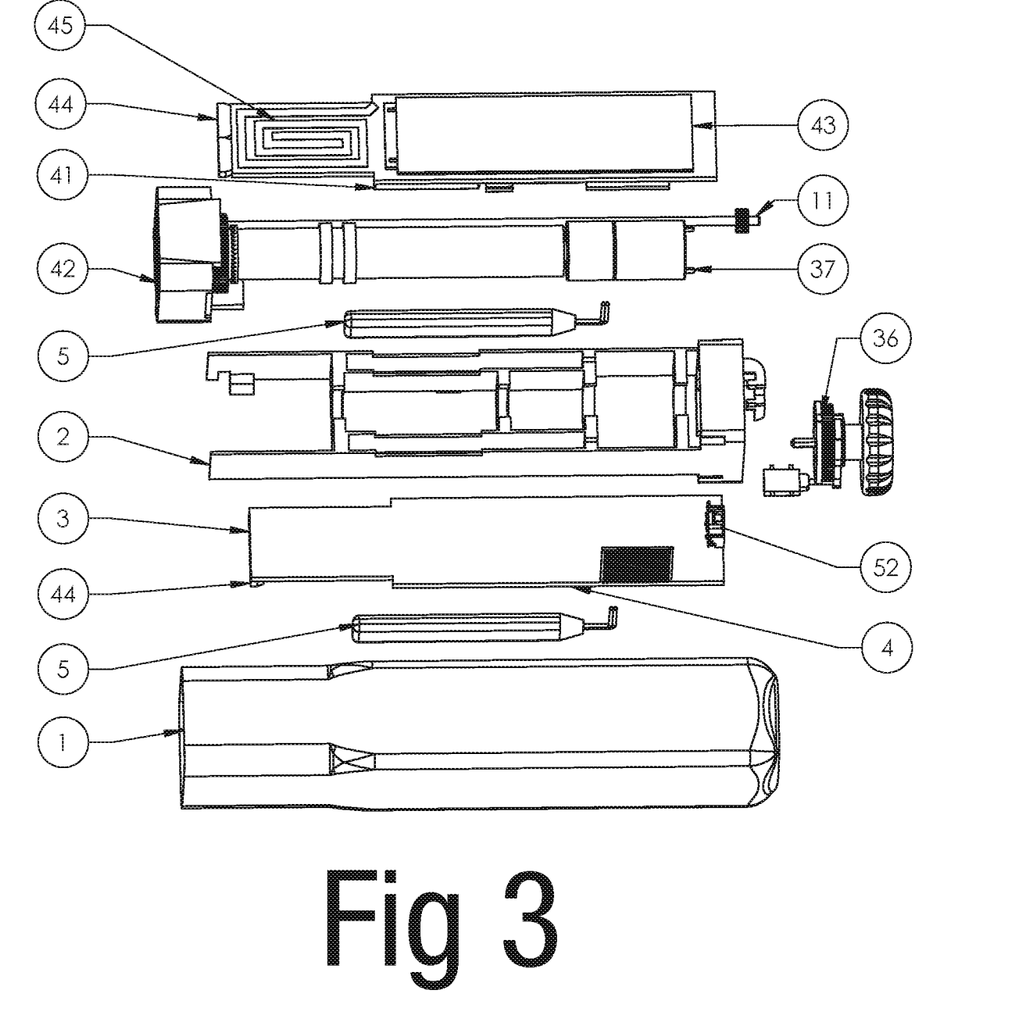
FIG. 3 is an exploded view of the pen injector base, illustrating the various components of the drive system and electronic control system, in accordance with an embodiment of the present technology.

FIG. 3 is an exploded view of the pen injector base 35. In some embodiments, a housing 2 fits within the shell 1. The housing 2 locates the main drive 37 centrally to the shell 1. In some embodiments, a printed circuit board 3 is affixed to the top and bottom of the housing 2. The printed circuit board 3 may contain the microcontroller 4, cell module 41, antenna 45, and a display 43. The microcontroller 4 will contain firmware to control internal and peripheral functions of the pen injector 100. In some embodiments, a battery 5 is placed on either side of the housing 2. The proximal end of the housing 2 positions the dosage select assembly 36 and the drive rod 11. In certain embodiments, the dial 6 is located centrally within the base 35, where the dial 6 is concentrically aligned with the main drive 37.

Figure 4:
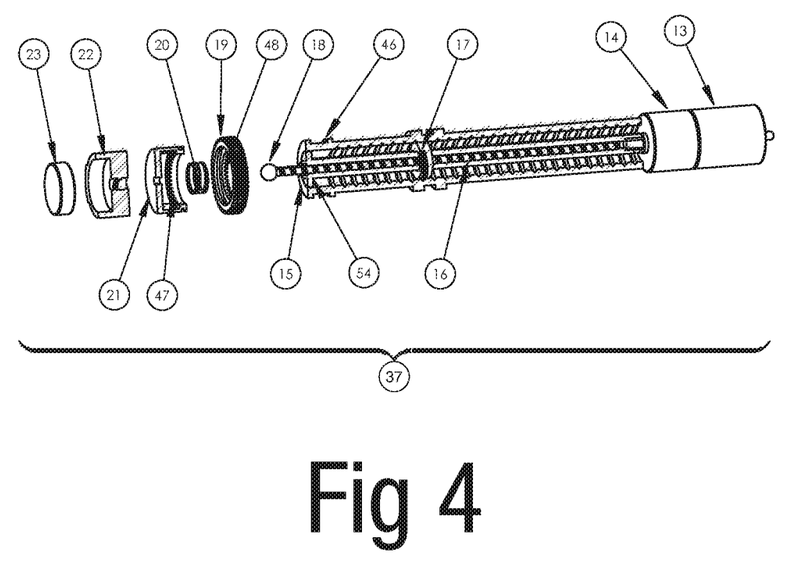
FIG. 4 is an exploded view of the main drive of the pen injector, in accordance with an embodiment of the present technology.

FIG. 4 is a front-side exploded view of the main drive 37. In some embodiments, an electric direct current (DC) motor 13 is fixed to a gearbox 14. In other embodiments, the DC motor 13 is a stepper motor, which may or may not make use of a gearbox 14. The gearbox 14 is secured to the motor coupler 16 with an output shaft. In certain embodiments, the lead screw 18 is fixed radially within the motor coupler 16 but can translate axially. In certain embodiments, the dosage stop 17 is fixed radially around the motor coupler 16. The dosage stop 17 is threaded to engage the internal threading of the dosage select coupler 15, which dictates the position of the dosage stop 17. At its distal-most position, the dosage stop 17 binds with the actuator stop 54 on the distal end of the motor coupler 16, which creates a mechanical limit of the motor 13, and limits the linear motion of the lead screw 18. In some embodiments, there is a selection gear 19 which is positioned concentrically to the dosage select 15 and is bound distally and proximally by the dosage select teeth 46. The selection gear 19 is fixed axially to the dosage select engage 21 and is biased distally from the compression spring 20. The dosage select engage 21 is fixed radially to the lead screw 18. The lead screw nut 22 is fixed radially and limited axially at its distal-most position by the cartridge connect 42. The internal threading on the lead screw nut 22 engages the threading of the lead screw 18 to drive the lead screw 18 distally and proximally within the injector base 35. The distal end of the lead screw 18 is fixed to the plunger head 23, which drives the movable plunger 302 within the cartridge 300.

Figure 5:
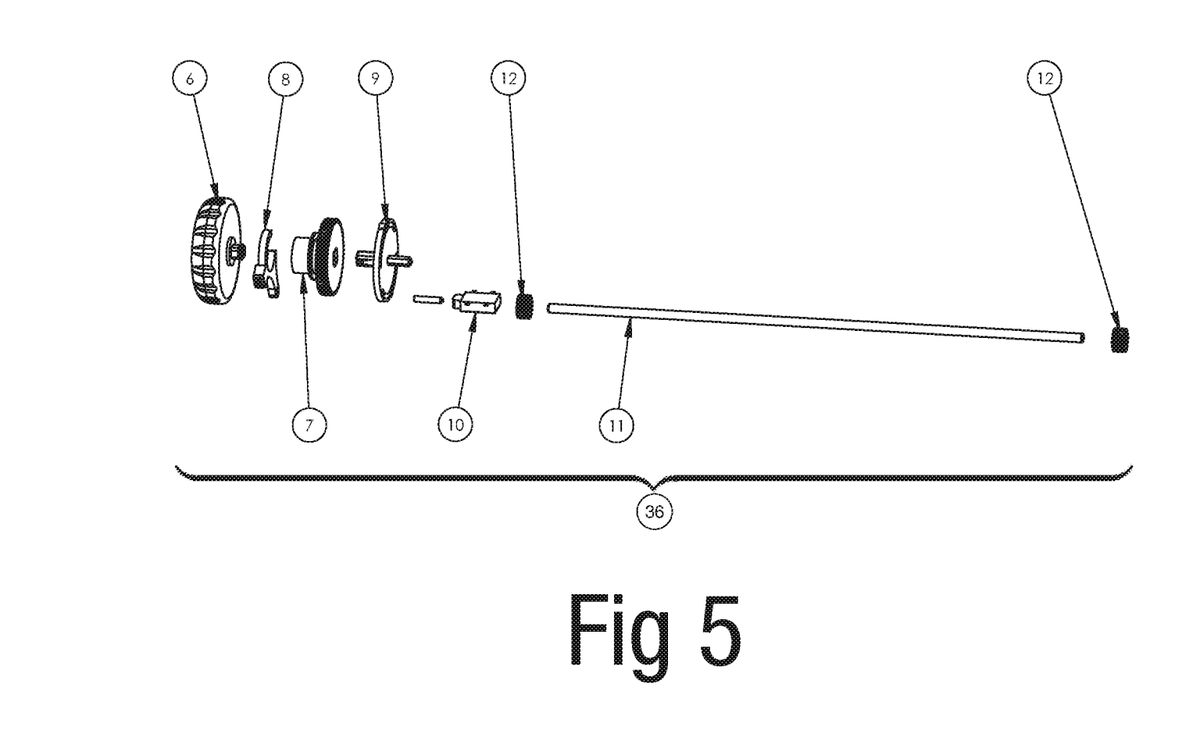
FIG. 5 is an exploded view of the dosage select assembly of the pen injector, in accordance with an embodiment of the present technology.

FIG. 5 is a front-side exploded view of the dosage select assembly 36. In certain embodiments, the dial 6 is rigidly fixed to the dosage select gear 7. The dial 6 can move axially, providing at least two distinct positions and can rotate radially to allow further user input. The drive engage 8 is axially fixed to the dosage select gear 7. In the distal position, when the dial 6 is at its innermost position, the drive engage 8 engages the tactile button 10. In some embodiments, the tactile button can be another type of activation switch (e.g. a button, toggle, lever, dial, rocker or similar). The dosage select gear 7 is disengaged from the drive rod gear 12. In certain embodiments, the teeth on the drive engage 8 engage with the drive rod gear 12 fixing the drive rod 11. In certain embodiments, in the proximal position, the teeth on the drive engage 8 disengage from the drive rod gear 12, and the dosage select gear 7 engages with the drive rod gear 12. In this way, the radial position of the dial 6 dictates the radial position of the drive rod 11, which in turn dictates the position of the selection gear 19. In certain embodiments, the tactile knob 9 is radially fixed to the dosage select gear 7. The tactile knob 9 is fixed axially to the housing 2, where it engages the housing 2 to provide a tactile feedback to the user as the dial 6 is rotated. In certain embodiments, the tactile knob 9 is radially fixed to a rotary encoder 52, which translates the motion of the dial 6 to the microcontroller 4.

In referring to FIGS. 2-4 together, a control system comprises a microcontroller 4 running firmware for operating the drug delivery assembly 101. In certain embodiments, the firmware on the microcontroller 4 calculates the linear position of the main drive 37 through a rotary encoder 52. In other embodiments, the linear position is calculated using a linear potentiometer design, were the shell 1 or shell housing 2 contains a conductive strip and the lead screw 18 will contain a wiper. The firmware uses the linear potentiometer or rotary encoder 52 input to control the linear position of the lead screw 18 via a closed loop control system (e.g. discrete proportional-integral-derivative (PID) or state space, single-input single-output (SISO) or multiple-input multiple-output (MIMO), feedforward, feedback, or a combination thereof, etc.). In other embodiments, the linear position of the main drive 37 is determined through a feed forward control, where the position may be determined from the back electromotive force (back-EMF) voltage. In certain embodiments, a combination of feedforward and feedback control is used. In some embodiments, a stepper motor is used instead of the direct DC motor 13. When a stepper motor is used, direct stepping of the motor takes the place of the feedforward control loop.

In certain embodiments, the firmware on the microcontroller 4 sends and receives data/commands to and from the cellular module 41. The microcontroller 4 may communicate with the cellular module 41 using standard communication protocols (e.g. I2C, universal asynchronous receiver/transmitter (UART), serial peripheral interface (SPI), etc). In some embodiments, the display 43 is controlled by the microcontroller 4 using standard communication protocols (e.g. I2C, UART, SPI, etc). In certain embodiments, the firmware on the microcontroller 4 has internal interrupt capabilities for a limit switch, tactile button 10 input from the dial 6, and/or from the rotary encoder 52. In certain embodiments, the firmware on the microcontroller 4 uses pulse width modulation to control the output pin for the motor 13 and at least three output pins for light emitting diodes (LEDs) that provide accent lighting 44.

In certain embodiments, the firmware on the microcontroller 4 utilizes an analog to digital converter to read in analog values from sensors. In certain embodiments, a skin sensor (e.g. touch capacitive, resistive, mechanical, etc.) is used to determine contact with the user's skin. In some embodiments, a temperature sensor is used to determine the temperature of the loaded cartridge 25. In some embodiments, an accelerometer, magnetometer, gyroscope or some combination thereof is used to determine the acceleration and orientation of the pen injector 100.

In referring to FIGS. 4 and 5 together, the main drive 37 and dosage select assembly 36 are reversibly coupled. In certain embodiments, the dosage select engage teeth 48 bind with the dosage select teeth 46 when the selection gear 19 is in the distal position due to the bias of the compression spring 20, fixing the dosage select engage 21 radially with the dosage select 15. In this manner, as the motor coupler 16 rotates, the dosage select coupler 15 rotates as well, causing the dosage stop 17 to remain fixed axially as the lead screw 18 rotates. This allows the lead screw 18, and therefore the plunger head 23 to move axially without the dosage stop 17 binding with the motor coupler 16. When the plunger head 23 engages the plunger 56 within the cartridge 25, the force exerted on the plunger 56 is translated to the lead screw nut 22. In certain embodiments, when the force exerted on the lead screw nut 22 exceeds the force from the compression spring 20, the dosage select engage teeth 47 disengage from the dosage select teeth 46, and the selection gear coupling teeth 48 bind with the dosage select teeth 46. In this way, the dosage select 15 moves with the selection gear 19. The rotation of the selection gear 19 is dictated by the rotation of the drive rod 11. The rotation of the selection gear 19 then dictates the position of the dosage stop 17, and is set through user input.

Selected Examples of Pen Caps and Related Devices and Methods

Figure 6:
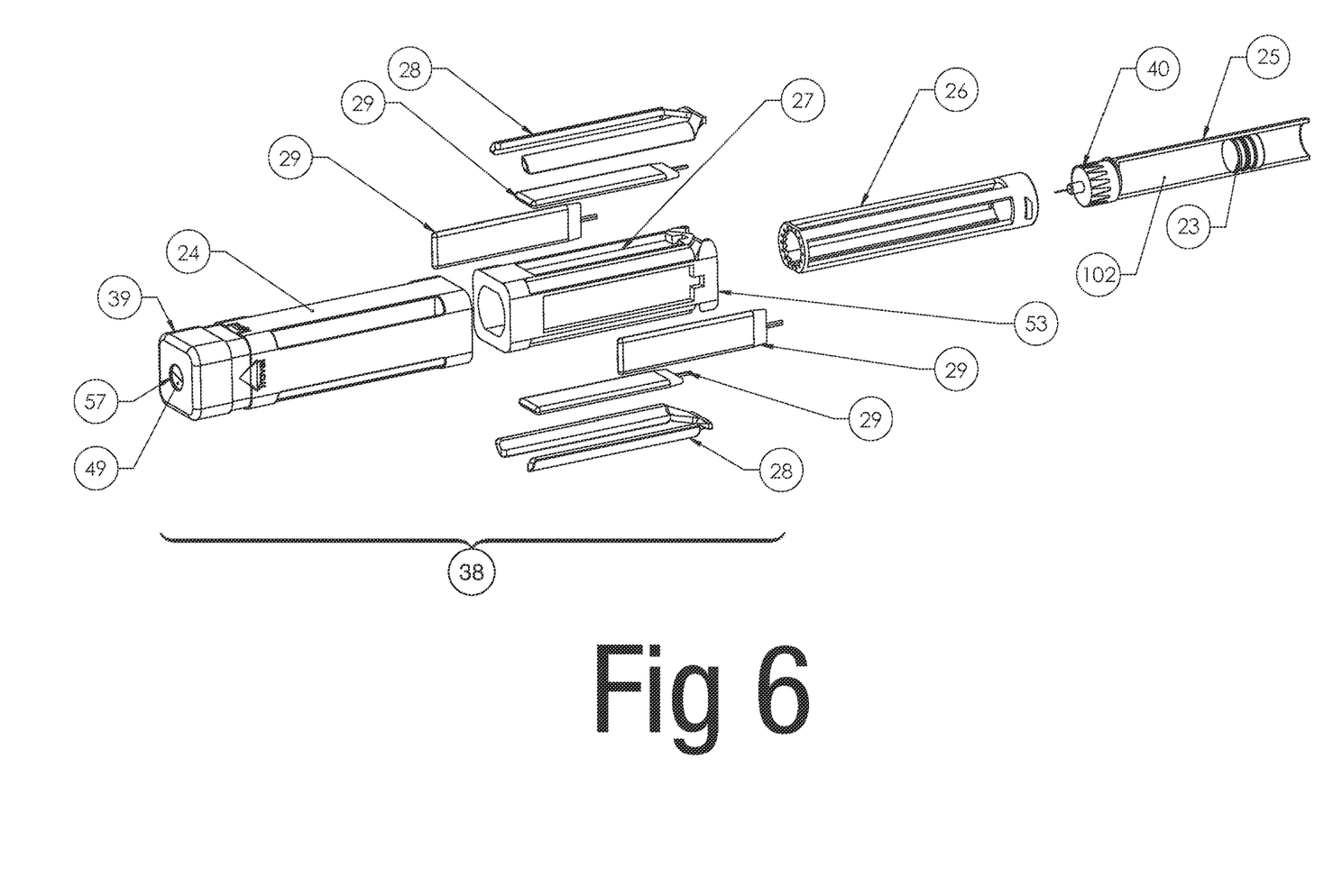
FIG. 6 is an exploded view of the pen cap, cartridge holder and the medicament-filled cartridge, in accordance with an embodiment of the present technology.

FIG. 6 is a front-side exploded view of the pen cap 38, cartridge 300 and cartridge case 26, in accordance with an embodiment of the present technology. On the proximal end of the pen cap 38, base connect 53 provides physical connection to the cap connect 55 on the distal end of the base 35. In certain embodiments, the physical interaction between the base connect 53 and cap connect 55 forms mechanical and electrical connections between the pen cap 38 and pen injector 100. In certain embodiments, base connect 53 is located on the cap shell 24. In other embodiments, base connect 53 is located on the cap housing 27. The cap housing 27 is located within the cap shell 24. In certain embodiments, the cap housing 27 contains one or more supplementary cap batteries 29. In certain embodiments, the cap batteries 29 act as a power reservoir for the base 35 to extend the pen injector's 100 overall battery life. In further embodiments, the cap batteries 29 power electrical components in the pen cap 38, such as sensors or wireless communication modules. In some embodiments, cap lighting 28 is incorporated into the cap housing 27, where the accent lighting 44 light passes through and causes the cap lighting 28 to become illuminated. In some embodiments, the cartridge case 26 and shell housing 27 have one or more flattened sides to ensure that the top is radially oriented with the base 35. In some embodiments, the distal-most end of the cap 38 houses a needle insertion/retraction mechanism 39. The needle insertion/retraction mechanism 39 is fixed to the cap shell 24.

Figure 7:
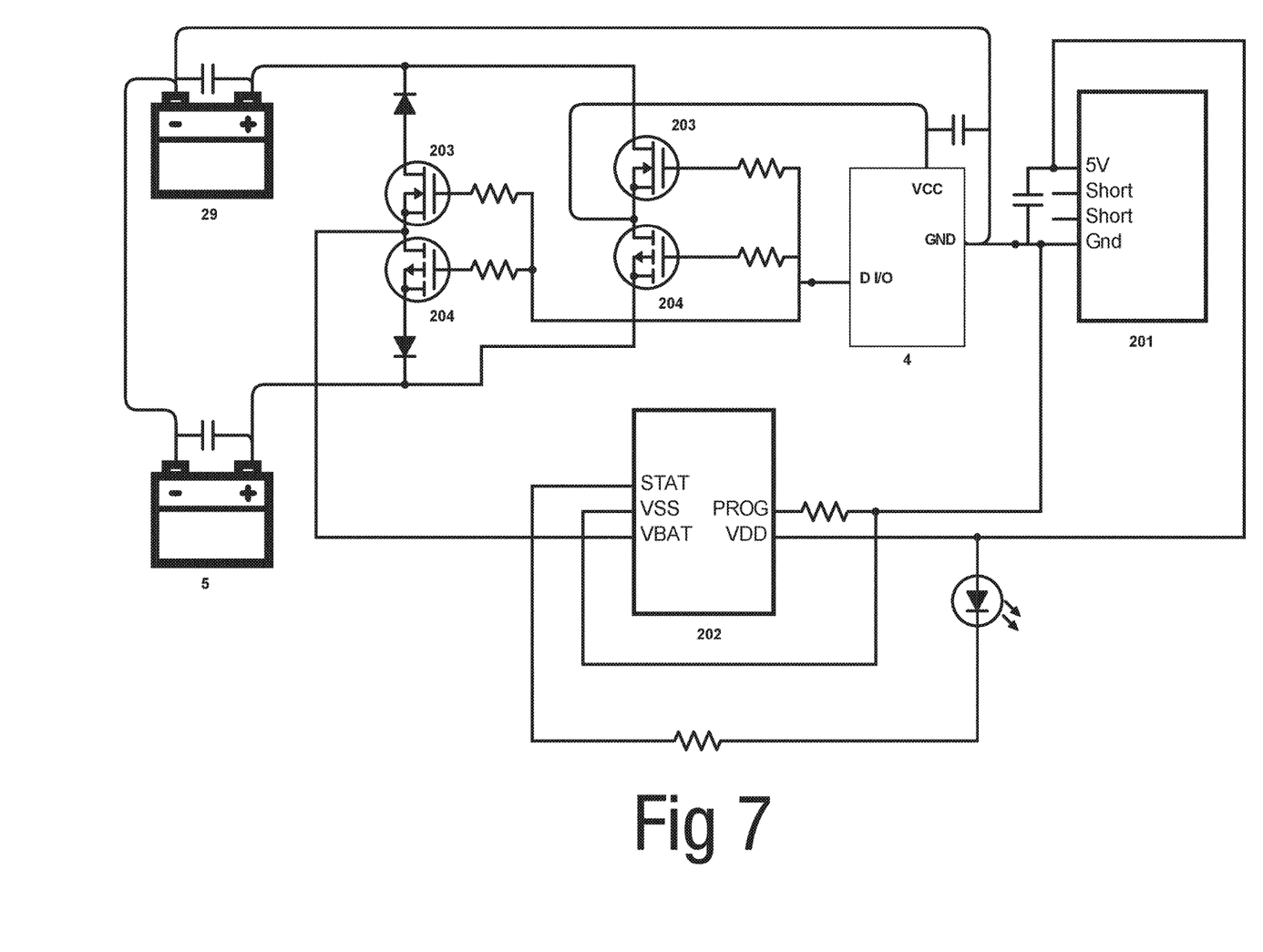
FIG. 7 is a schematic view of an electrical circuit formed when the pen cap is operatively connected to the pen injector, in accordance with an embodiment of the present technology.

FIG. 7 is a schematic view of an electrical circuit formed when the pen cap 38 is operatively connected to the pen injector 100, in accordance with an embodiment of the present technology. This schematic is in reference to the charging and discharging of the injector battery 5 and the cap battery 29 to power the microcontroller 4 and other peripherals (e.g. motor 13, etc.) of the drug delivery assembly 101. In certain embodiments, a digital input, output pin on the microcontroller 4 controls a series of P-channel 204 and N-channel 203 MOSFETs to dictate the flow of electricity. For the charging, power is supplied from the regulated power supply 201 to the battery charging integrated circuit 202. In certain embodiments, the integrated circuit 202 provides power to the source of the P-channel MOSFET 304 and the drain of the N-Channel MOSFET 203. When the MOSFET gates are pulled low from the microcontroller 4, the battery charging integrated circuit 202 charges the injector battery 5, and when the MOSFET gates are pulled high, the battery charging integrated circuit 202 charges the cap battery 29. In certain embodiments, the battery charging integrated circuit 202 uses feedback to determine the charge state (e.g. voltage level, battery temperature, etc.) and communicates to the microcontroller 4 with standard protocols (e.g. I2C, SPI, UART, etc.). In some embodiments, two pull down resistors to two analog input pins on the microcontroller 4 are utilized to determine the charge of both the injector battery 5 and cap battery 29. The resistors are placed at the positive terminal of each battery. In other embodiments, two battery power level integrated circuits are placed at the positive terminal of both the injector battery 5 and the cap battery 29 to determine the battery charge level. In certain embodiments, the injector battery 5 supplies power to the source of the P-channel MOSFET 204 and the cap battery 29 supplies power to the drain of the N-channel MOSFET 203 for powering the microcontroller 4 and peripherals. When the MOSFET gates are pulled low from the microcontroller 4, the injector battery 5 supplies the power to the microcontroller 4 and peripherals, and when the MOSFET gates are pulled high, the cap battery 29 supplies the power. In some embodiments, a voltage regulator is included to ensure the proper voltage is supplied to the microcontroller 4 and the peripherals. In certain embodiments, a capacitor is placed after the MOSFETs to smooth voltage drops and spikes during the MOSFET switching in order to provide consistent power to the microcontroller 4 and peripherals.

Figure 8:
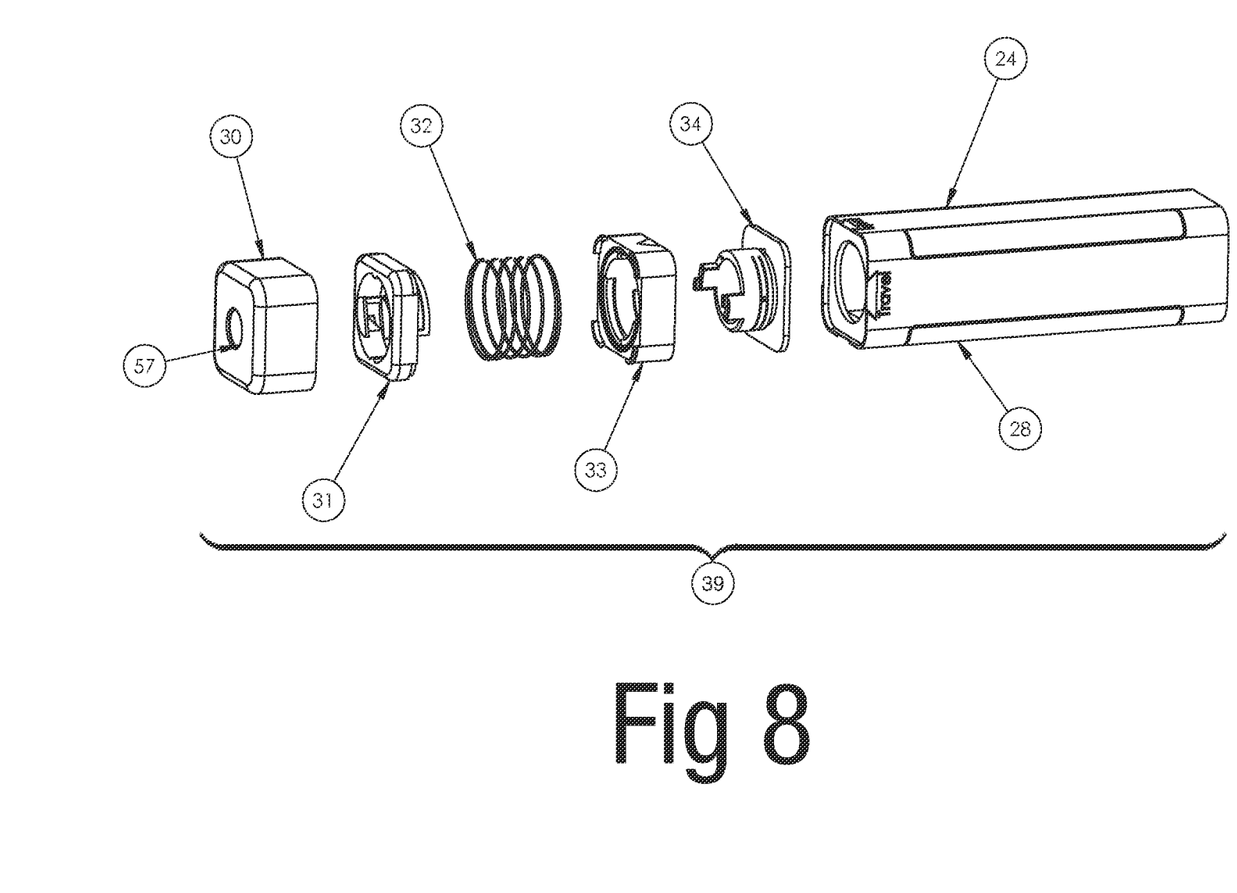
FIG. 8 is an exploded view of the needle insertion/retraction mechanism of the pen cap, in accordance with an embodiment of the present technology.

FIG. 8 is a front-side exploded view of the needle insertion/retraction mechanism 39, in accordance with an embodiment of the present technology. In some embodiments, the lock engage 34 is rigidly attached to the distal end of the cap shell 24. The lock cover 33 is axially fixed to the lock engage 34. In certain embodiments, the lock cover 33 is radially constrained to rotate a quarter turn relative to the lock engage 34. The shield and lock 31 is biased distally from the lock cover 33 by the cap spring 32. The shield and lock 31 is rigidly attached to the cap end 30. The cap end 30 is radially constrained to the lock cover 33. The cap end 30 is axially constrained at its distal-most position by the lock cover 33.

Figure 9A:
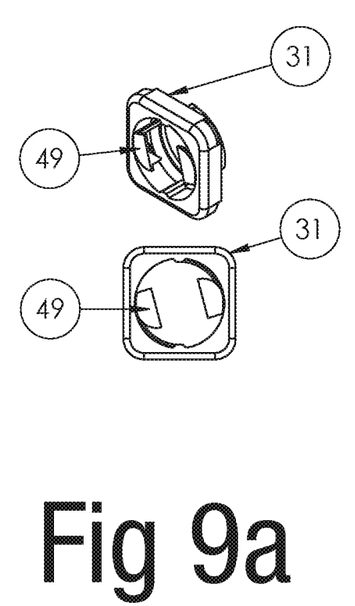
FIGS. 9A and 9B show the shield and lock of the needle insertion/retraction mechanism in an open position and a closed position, respectively, in accordance with an embodiment of the present technology.
Figure 9B:
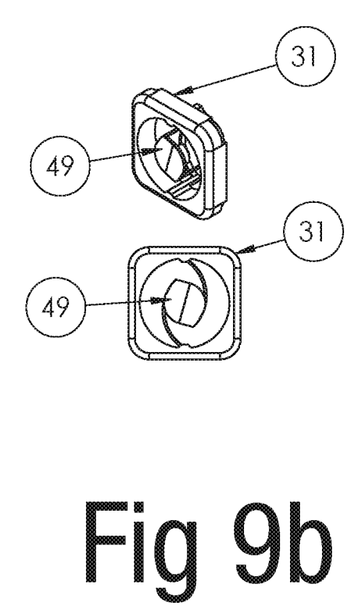

FIGS. 9A and 9B show the shield and lock 31 in an open position and a closed position, respectively. In certain embodiments, the shield and lock 31 contains, or is assembled to, two shield and lock arms 49. When the shield and lock 31 is in an open position, the needle 40 can pass through the needle aperture 57 on the cap end 30. When the shield and lock 31 is in a closed position, the arms 49 are covering the needle aperture 57, preventing the needle 40 from passing through. In certain embodiments, the arms 49 are biased inwards. When the shield and lock 31 is in a closed position, the arms 49 are in the inward position (FIG. 9A), where they come together to form a door that covers the aperture in the shell end 30. The arms 49 in the inward position also interfere with the distal edge of the lock engage, locking the needle insertion/retraction mechanism 39 in the distal position. In certain embodiments, when the needle insertion/retraction mechanism 39 is rotated a quarter turn, the arms of the lock engage 34 push the shield and lock arms 49 outward, exposing the aperture in the shell end 30 (FIG. 9B). Additionally, the arms 49 get pushed beyond the distal edge of the lock engage 34, and no longer cause interference with the lock engage 34, allowing the shield and lock 31 and shell end 30 to move proximally when the force applied to the shell end 30 exceeds the cap spring 32 force. In some embodiments, the shield and lock arms are shaped in such a way that allow them to separate by the needle cap 51, if the cap 38 is placed on the pen injector 100 while the needle cap 51 is still covering the needle 40.

In referring to FIGS. 1A-9B together, the pen injector 100 can be operated with the pen cap 38 operatively connected, forming a drug delivery assembly 101. The user can perform a single injection by sequentially (a) disconnecting the pen cap 38 from the base 35, (b) attaching a needle 40 to the distal end of the cartridge 300, (c) connecting the pen cap 38 to the base 35, (d) setting a dose using the dial 6, (e) unlocking the needle insertion/retraction mechanism 39, (f) pressing the distal end of the pen cap 30 downward onto the injection site, and (g) pressing the activation button. In certain embodiments, the dial 6 is the activation button. In other embodiments, the dial 6 is supplemented with a separate activation switch (e.g. a button, toggle, lever, dial, rocker or similar), where the activation switch has binary user input. In further embodiments, there is no user-facing activation switch. In these embodiments, there is an activation switch within the needle insertion/retraction mechanism 39. In these embodiments, the user commences the injection process by overcoming the force of the cap spring 32, triggering the activation switch.

Embodiments of the present disclosure include various steps and operations, which have been described above. A variety of these steps and operations may be performed by hardware components or may be embodied in machine-executable instructions, which may be used to cause a general-purpose or special-purpose processor (e.g., microcontroller 4) programmed with the instructions to perform the steps. Alternatively, the steps may be performed by a combination of hardware, software, and/or firmware. The instructions may be stored in a non-transitory storage medium, such as random access memory (RAM), read only memory (ROM), or any other storage device(s) commonly known in the art. Read only memory can be any static storage device(s) such as Programmable Read Only Memory (PROM) chips for storing static information, such as instructions for the microcontroller 4.

The components described above are meant to exemplify some types of possibilities. In no way should the aforementioned examples limit the disclosure, as they are only exemplary embodiments.

Terminology

Brief definitions of terms, abbreviations, and phrases used throughout this application and the appendices are given below.

The terms "connected" or "coupled" and related terms are used in an operational sense and are not necessarily limited to a direct physical connection or coupling. Thus, for example, two devices may be coupled directly or via one or more intermediary media or devices. As another example, devices may be coupled in such a way that information can be passed therebetween, while not sharing any physical connection with one another. Based on the disclosure provided herein, one of ordinary skill in the art will appreciate a variety of ways in which connection or coupling exists in accordance with the aforementioned definition.

The phrases "in some embodiments," "according to some embodiments," "in the embodiments shown," "in other embodiments," "in certain embodiments," "embodiments," and the like generally mean that the particular feature, structure, or characteristic following the phrase is included in at least one embodiment of the present disclosure and may be included in more than one embodiment of the present disclosure. In addition, such phrases do not necessarily refer to the same embodiments or to different embodiments.

If the specification states a component or feature "may," "can," "could," or "might" be included or have a characteristic, that particular component or feature is not required to be included or have the characteristic.

The term "module" refers broadly to a software, hardware, or firmware (or any combination thereof) component. Modules are typically functional components that can generate useful data or other output using specified input(s). A module may or may not be self-contained.

In conclusion, the present disclosure discloses novel systems, methods, and arrangements for delivering medicaments. While detailed descriptions of one or more embodiments of the disclosure have been given above, various alternatives, modifications, and equivalents will be apparent to those skilled in the art without varying from the spirit of the disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof. Therefore, the above description should not be taken as limiting.

We claim:

1. A drug delivery system comprising:
    a pen cap;
    a pen injector, comprising:
        a medicament-filled cartridge including a movable plunger at the proximal end and an outlet at the distal end;
        a housing for the cartridge that centrally aligns the movable plunger with a drive mechanism;
        an electromechanical drive mechanism for dispensing the medicament through the cartridge outlet, comprising:
            a motor coupled to a control system; and
            a linear actuator coupled to the motor;
        an electronic control system for processing information and controlling operations of the drug delivery system, comprising:
            a processor coupled to one or more sensors; at least one battery for powering the processor; and
            non-volatile memory for storing information and programs related to the operations of the drug delivery assembly;
        a dose setting mechanism for selecting the amount of medicament to be dispensed and communicating the amount to the electronic control system, comprising:
            a dosage select mechanism for increasing or decreasing the amount of medicament selected to be dispensed;
            a dosage select sensor for detecting movement of the dosage select mechanism and communicating the selected dose to the electronic control system; and
            a dosage select gear; and
        a dose limiting mechanism for preventing the electromechanical drive mechanism from dispensing more medicament than was selected, wherein the dosage select gear reversibly couples the dosage select mechanism to the dosage select sensor and the dose limiting mechanism, the dose limiting mechanism comprising:
            a dosage stopper operably coupled to the linear actuator of the electromechanical drive mechanism and the dose setting mechanism;
            a drive mechanism coupler for reversibly connecting the dosage stopper to the linear actuator of the electromechanical drive mechanism;
            a dose setting mechanism coupler for reversibly connecting the dosage stopper to the dose setting mechanism; and
            an actuator stopper axially aligned with the dosage stopper for physically limiting linear movement of the linear actuator during each injection.

2. The system of claim 1, wherein the motor drives the axial movement of the linear actuator.

3. The system of claim 1, wherein the motor is an electric motor.

4. The system of claim 1, wherein the linear actuator is a lead screw.

5. The system of claim 1, wherein the electronic control system communicates with one or more peripheral sensors.

6. The system of claim 5, wherein at least one of the one or more peripheral sensors detects the output of the motor.

7. The system of claim 5, wherein at least one of the one or more peripheral sensors detects the position of the linear actuator.

8. The system of claim 5, wherein at least one of the one or more peripheral sensors detects contact between the linear actuator and the movable plunger of the medicament-filled cartridge.

9. The system of claim 1, wherein the dosage select mechanism of the dose setting mechanism comprises a mechanical dosage select mechanism.

10. The system of claim 1, wherein the dosage select mechanism is rotatable around a central axis.

11. The system of claim 10, wherein the dosage select sensor detects the degree of rotation of the dosage select mechanism.

12. The system of claim 1, wherein the dosage select mechanism is slidable along a linear axis.

13. The system of claim 12, wherein the dosage select sensor detects the distance of linear displacement of the dosage select mechanism.

14. The system of claim 1, wherein the dosage stopper of the dose limiting mechanism comprises a mechanical dosage stopper assembly.

15. The system of claim 1, wherein the dosage stopper is coupled to at least one of the dose setting mechanism or the drive mechanism.

* * * * *